United States Patent
Hendrix et al.

(10) Patent No.: US 7,027,158 B2
(45) Date of Patent: Apr. 11, 2006

(54) BEAM SPLITTER/COMBINER FOR OPTICAL METEROLOGY TOOL

(75) Inventors: James Hendrix, Livermore, CA (US); David Wang, Fremont, CA (US); Michael Ellison, Boulder, CO (US); Joel Ng, San Leandro, CA (US)

(73) Assignee: Therma-Wave, Inc., Fremont, CA (US)

( * ) Notice: Subject to any disclaimer, the term of this patent is extended or adjusted under 35 U.S.C. 154(b) by 484 days.

(21) Appl. No.: 10/229,630

(22) Filed: Aug. 28, 2002

(65) Prior Publication Data

US 2003/0169425 A1  Sep. 11, 2003

Related U.S. Application Data

(60) Provisional application No. 60/363,110, filed on Mar. 11, 2002.

(51) Int. Cl.
*G01N 21/45* (2006.01)

(52) U.S. Cl. ...................... 356/445; 356/369
(58) Field of Classification Search ............... 356/445, 356/364–369, 618, 629, 583, 634
See application file for complete search history.

(56) References Cited

U.S. PATENT DOCUMENTS

| | | | | |
|---|---|---|---|---|
| 3,586,851 A | * | 6/1971 | Rudolph | 362/293 |
| 3,711,700 A | * | 1/1973 | Westlund et al. | 362/293 |
| 5,260,578 A | * | 11/1993 | Bliton et al. | 250/461.1 |
| 5,360,659 A | * | 11/1994 | Arends et al. | 428/216 |
| 5,798,837 A | | 8/1998 | Aspnes et al. | 356/369 |
| 5,882,774 A | * | 3/1999 | Jonza et al. | 428/212 |
| 6,463,084 B1 | * | 10/2002 | Govorkov et al. | 372/9 |
| 6,788,404 B1 | | 9/2004 | Lange | 356/237.2 |
| 2004/0012774 A1 | | 1/2004 | Lange | 356/237.1 |

* cited by examiner

*Primary Examiner*—Layla G. Lauchman
(74) *Attorney, Agent, or Firm*—Stallman & Pollock LLP

(57) ABSTRACT

A combiner for optical beams includes a substrate overlaid by a multi-layer dielectric film stack. The substrate is a clear material and the dielectric film stack is a series of alternating layer of high and low refractive index. This gives the combiner relatively high reflectivity across UV wavelengths and relatively high transmissivity in the visible and longer wavelengths and allows visible light to pass through the combiner while UV light is reflected. At the same time dielectric film stack has minimal absorption and scatter. This means that the intensity of visible light maintains at least 90% of its intensity as it passes through combiner and UV light retains at least 90% of its intensity as it is reflected by combiner.

27 Claims, 3 Drawing Sheets

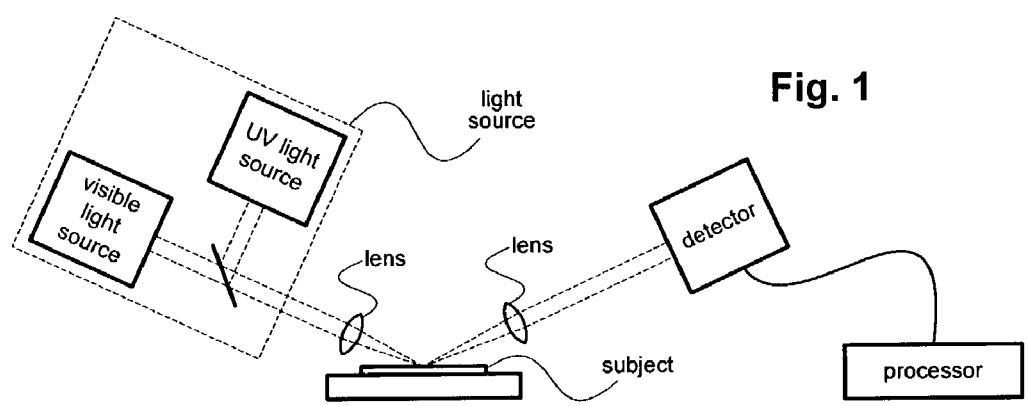
Fig. 1
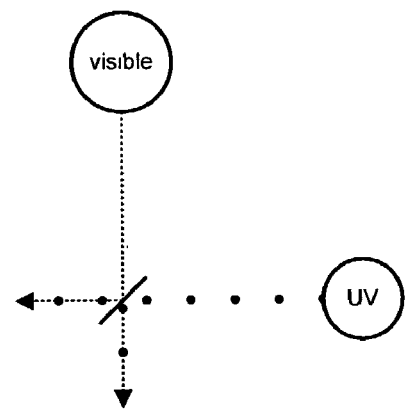
Fig. 2
Fig. 3
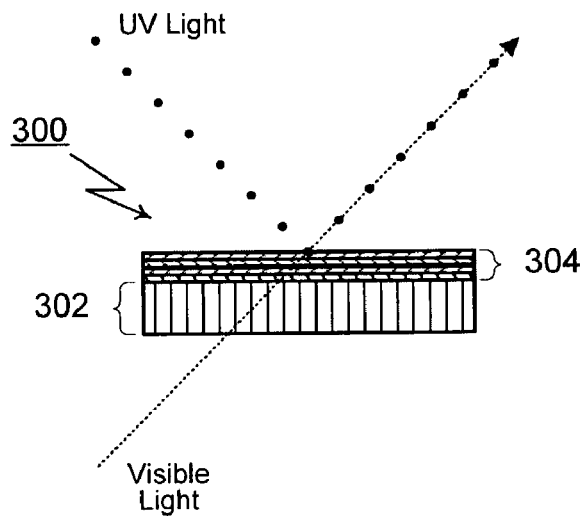

BEAM SPLITTER/COMBINER FOR OPTICAL METEROLOGY TOOL

PRIORITY CLAIM

The present application claims priority to U.S. Provisional Patent Application Ser. No. 60/363,110, filed Mar. 11, 2002, which is incorporated herein by reference.

TECHNICAL FIELD

The subject invention relates to a device for combining two beams of light with minimal loss to create a single output beam.

BACKGROUND OF THE INVENTION

Over the past several years, there has been considerable interest in using optical methods to perform non-destructive inspection and analysis of semi-conductor wafers. The type of inspection is commonly referred to as optical metrology and is typically performed using a range of related techniques including ellipsometry and reflectometry. At the heart of these techniques is the notion that a subject may be examined by analyzing the reflection of a probe beam that is directed at the subject. For the specific case of ellipsometry, changes in the polarization state of the probe beam are analyzed. Reflectometry is similar, except that changes in magnitude are analyzed. Ellipsometry and reflectometry are effective methods for measuring a wide range of attributes including information about thickness, crystallinity, composition and refractive index. The structural details of ellipsometers are described more fully in U.S. Pat. Nos. 5,910,842 and 5,798,837 both of which are incorporated in this document by reference.

Scatterometry is a related technique that measures the diffraction (optical scattering) that results when a probe beam is directed at a subject. Scatterometry is an effective method for measuring the critical dimension (CD) of structural features (such as the lines and other structures included in integrated circuits). Scatterometry can be used to analyze two periodic two-dimensional structures (e.g., line gratings) as well as periodic three-dimensional structures (e.g., patterns of vias or mesas in semiconductors). Scatterometry can also be used to perform overlay registration measurements. Overlay measurements attempt to measure the degree of alignment between successive lithographic mask layers.

Most metrology techniques (including those just described) may be performed using monochromatic or polychromatic light. In the case where polychromatic light is used, the interaction between the probe beam and the subject is analyzed as a function of wavelength. In many cases, this increases the accuracy of the analysis. As shown in FIG. 1, a representative implementation of an ellipsometer or reflectometer configured to perform this type of polychromatic analysis includes a broadband light source. The light source creates a polychromatic probe beam that is focused by one or more lenses on a subject. The subject reflects the probe beam. The reflected probe beam passes through another series of one or more lenses to a detector. A processor analyzes the measurements made by the detector.

The broadband light source is a combination of two different sources: a visible light source and a UV source. The visible light source is typically a tungsten lamp and the UV source is typically a deuterium lamp. The outputs of the two lamps are combined using a beam combiner. Prior art beam combiners are usually formed by depositing a very thin partially transparent metal film, such as aluminum on a substrate. The surface of the film is coated with a protective layer of silicon dioxide or magnesium fluoride. A notable example of a UV to visible beam combiner is a 50/50 beam splitter. The output of the beam combiner is the probe beam produced by the broadband light source. The combination of the two separate lamps increases the spectrum of the probe beam beyond what would be practical using a single source.

Unfortunately, the use of prior art beam combiners has known drawbacks. As shown in FIG. 2, a portion of the beam produced by the visible light source is lost because it is reflected instead of being transmitted by the combiner. The output of the UV light source suffers the opposite fate. A portion of that beam is lost because it is transmitted instead of being reflected by the combiner. An additional portion of each beam is lost through absorption and scatter during interaction with the combiner. The overall result is that the intensity of the combined probe beam is significantly reduced when compared to the sum of the outputs produced by the visible and UV light sources. For a 50/50 beam combiner, the intensity of the combined probe beam can be 30% of the sum of the outputs produced by the visible and UV light sources.

For these reasons and others, a need exists for improved devices for combining optical beams. This need is especially important for metrology tools, which require the combination of multiple illumination sources to create wide spectrum polychromatic probe beams.

SUMMARY OF THE INVENTION

The present invention provides a combiner for optical beams. The beam combiner includes a substrate overlaid by a multi-layer dielectric film stack. The substrate is formed from a transparent material such as fused silica. The film stack is designed to provide relatively high reflectivity across the UV wavelengths and relatively high transmissivity in the visible and longer wavelengths. During normal operation, the combiner is positioned at the perpendicular intersection of two beams: a visible light beam and a UV light beam. In this position, the transmissivity of the combiner allows the visible light beam to pass unimpeded. The reflectivity of the combiner redirects the UV light beam to coaxially follow the visible light beam. The result is a single output beam that combines the UV and visible light beams. The film stack has minimal absorption and scatter so more than 90% of the visible and UV light beams are transferred to the output beam.

To create the required combination of transmissivity (for visible light) and reflectivity (for UV light) the dielectric film stack is configured to include alternating layers of high and low refractive index materials. For a representative embodiment, two series of layers are used. The first series includes a total of twenty-eight layers. The low refractive index layers in the first series are formed using silicon dioxide ($SiO_2$). Scandium oxide ($Sc_2O_3$) is used for the high refractive index layers. The second series in the first series includes a total of fourteen layers. The low refractive index layers in the second series are formed using magnesium fluoride ($MgF_2$). Aluminum oxide ($Al_2O_3$) is used for the high refractive index layers.

The combiner may also act as a beam splitter. When positioned in the path of a beam including both visible and UV light, the combiner produces two output beams. The first output beam includes the visible component of the input beam and the second includes the UV component.

BRIEF DESCRIPTION OF THE DRAWINGS

FIG. 1 is a diagram of an optical metrology system shown as a representative use for a beam combiner.

FIG. 2 is a diagram showing operation of a prior art beam combiner.

FIG. 3 is a diagram of a combiner for optical beams as provided by the present invention.

DETAILED DESCRIPTION OF THE PREFERRED EMBODIMENTS

Figure 4:
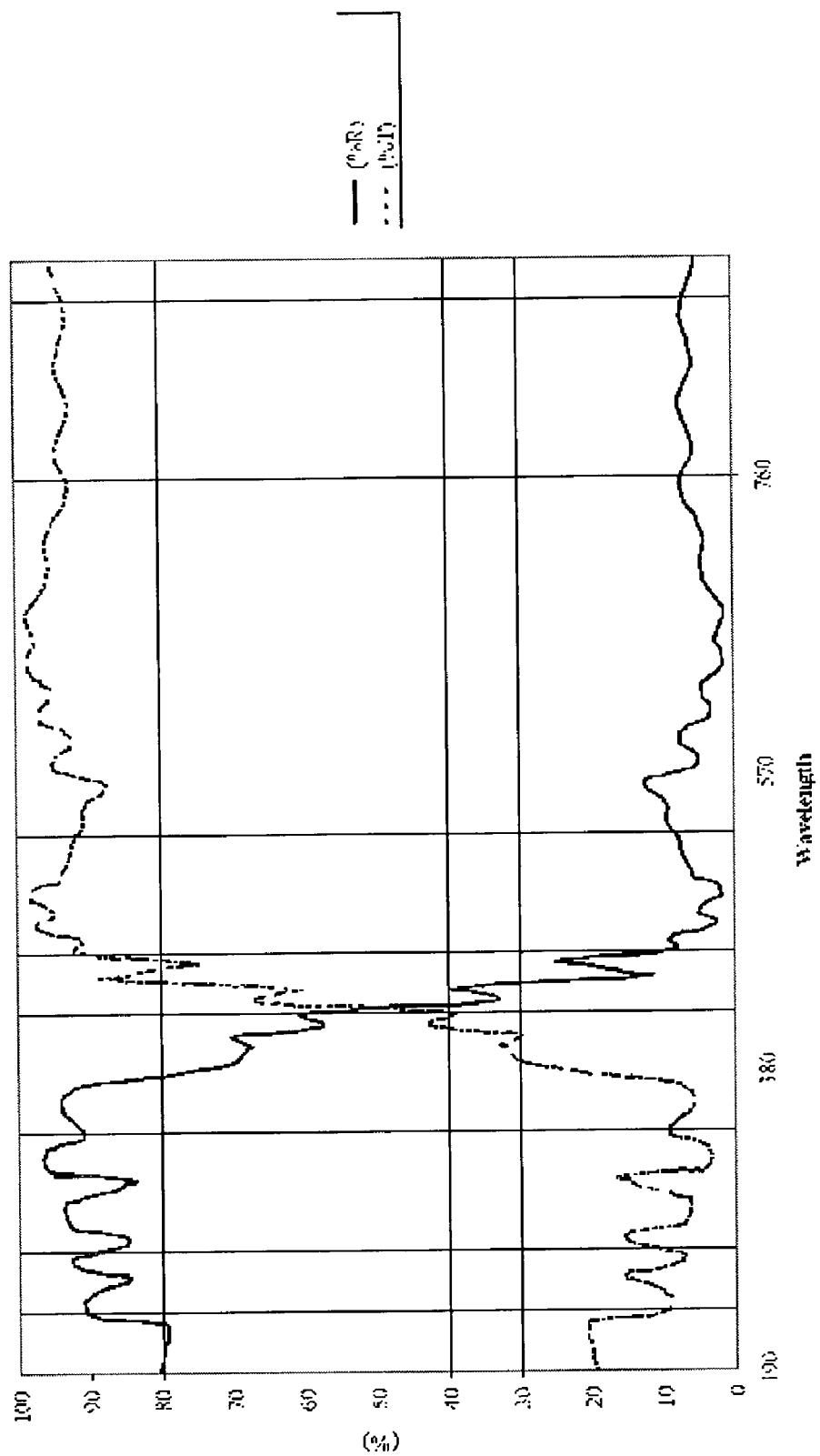
FIG. 4 is a plot of reflectivity and transmissivity as a function of wavelength for an embodiment of the combiner for optical beams provided by the present invention.

The present invention provides a combiner for optical beams. As shown in FIG. 3, a representative implementation of the combiner 300 includes a substrate 302 overlaid by a multi-layer dielectric film stack 304. Substrate 302 may be fabricated using a range of transparent materials. For the particular embodiment being described fused silica is used.

The film stack 304 is designed to provide relatively high reflectivity across UV wavelengths and relatively high transmissivity in the visible and longer wavelengths. As shown in FIG. 3, this allows visible light to pass through combiner 300 while UV light is reflected. At the same time dielectric film stack 304 has minimal absorption and scatter. This means that the intensity of visible light maintains at least 90% of its intensity as it passes through combiner 300. Similarly, UV light retains at least 90% of its intensity as it is reflected by combiner 300.

To create the required combination of transmissivity (for visible light) and reflectivity (for UV light) dielectric film stack 304 is configured to include alternating layers of high and low refractive index materials. For a representative embodiment, a total of twenty-eight layers are used (of which only four are shown in FIG. 3). Different embodiments may use more or less layers. The low refractive index layers are formed using silicon dioxide ($SiO_2$). Scandium oxide ($Sc_2O_3$) is used for the high refractive index layers.

Each of the layers within dielectric film stack 304 is typically formed with an approximate quarter-wave optical thickness. To reduce reflections in the visible and IR bands, it is possible to modify the thickness of individual layers within dielectric film stack 304. In practice, it has been found that one or more of the outer layers on each side of dielectric film stack 304 should be optimized in this fashion.

In practice, the combination of layers just described provides good reflectivity in the ultraviolet range above 215 nm. To increase this range, additional layers may be added at the top (non-substrate side) of dielectric film stack 304. For a representative embodiment, fourteen additional layers are added using magnesium fluoride ($MgF_2$) for the low refractive index layers and aluminum oxide ($Al_2O_3$) for the high refractive index layers. This provides good reflectivity in the ultraviolet range above 193 nm.

Other materials may be used for the additional layers including Neodymium Fluoride ($NdF_3$), Gadolinium Fluoride ($GdF_3$), Lanthanum Fluoride ($LaF_3$), Aluminum Oxide ($Al_2O_3$), Praseodymium Fluoride ($PrF_3$) and Thorium Fluoride ($ThF_4$) for the high refractive index layers and Aluminum Fluoride ($AlF_3$), Magnesium Fluoride ($MgF_2$), Silicon Dioxide ($SiO_2$), Lithium Fluoride (LiF), and Cryolite ($Na_3AlF_6$) for the low refractive index layers.

FIG. 4 shows a plot of reflectivity and transmissivity as a function of wavelength for the described embodiment of twenty-eight initial layers with fourteen additional layers. As shown in FIG. 4, reflectivity is high (and transmissivity is low) within the UV range of 180 to 350 nm. Within the visible range of 400 to 800 nm, reflectivity is low (and transmissivity is high).

Figure 5:
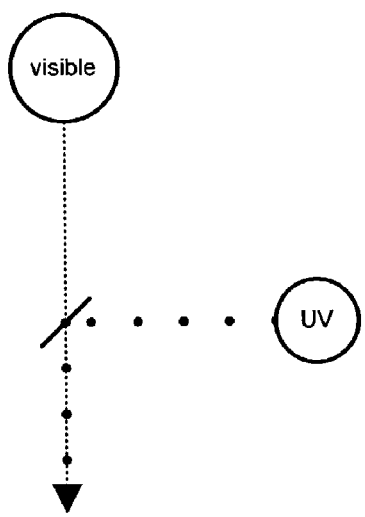
FIG. 5 is a diagram showing the combiner of the present invention being used to combine optical beams.

As shown in FIG. 5, the combiner 300 typically is positioned in the path of two beams: a visible light beam and a UV light beam. For most applications, these beams are mutually perpendicular and coplanar and the combiner 300 is positioned at their intersection. In this position, the transmissivity of the combiner 300 allows the visible light beam to pass unimpeded. The reflectivity of the combiner 300 redirects the UV light beam to coaxially follow the visible light beam. The result is a single output beam that combines the UV and visible light beams. The minimal absorption and scatter of the dielectric film stack 304 means that more than 90% of the visible and UV light beams is transferred to the output beam.

For typical optical metrology applications, the UV light beam of FIG. 5 is generated by a deuterium lamp. The visible light beam can be provided by a tungsten, xenon or halogen lamp. In order to create light into the infrared, a halogen lamp is used. For the specific combination of a deuterium lamp with a halogen lamp there is a known drop in intensity around the 400 nm region. For cases of this type, the layers within dielectric film stack 304 are reconfigured to reduce transmission and reflection above and below 400 nm in order to smooth out the intensity level of the beam across the entire wavelength range.

Figure 6:
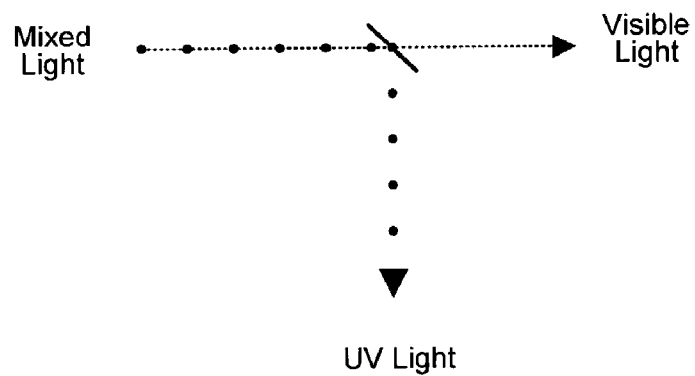
FIG. 6 is a diagram showing the combiner of the present invention being used to split an optical beam.

As shown in FIG. 6, the combiner 300 may also act as a beam splitter. When positioned in the path of a mixed beam including both visible and UV light, the combiner produces two output beams. The first output beam includes the visible component of the input beam and the second includes the UV component. In optical metrology tools, the type of configuration is particularly useful for splitting the light that has been reflected by the subject. Each separate component may then be passed to a separate detector.

In the preceding discussion, particular attention has been devoted to the use of combiner 300 within optical metrology tools. There are, of course, a wide range of systems of all types that use optical components. Combiner 300 is specifically intended to be useful across this range of systems and is not intended to be limited to the field of optical metrology.

What is claimed is:

1. A light source for an optical metrology tool which comprises:
    a first source producing a broadband visible light beam;
    a second source producing a broadband ultraviolet light beam; and
    a beam combiner positioned in the path of the visible and ultraviolet light beams, the beam combiner including a multilayer dielectric film stack, the multilayer dielectric film stack being substantially transmissive to light within the visible spectrum so that the broadband visible light beam is transmitted through the combiner, the multilayer dielectric film stack being substantially reflective to light within the ultraviolet spectrum so that the broadband ultraviolet light beam is reflected to follow the visible light beam.

2. A light source as recited in claim 1 wherein the multilayer dielectric film stack includes a first series of alternating layers of high and low refractive index materials.

3. A light source as recited in claim 2 wherein the layers within the first series of high refractive index materials are composed of scandium oxide ($Sc_2O_3$) and the layers within the first series of low refractive index materials are composed of silicon dioxide ($SiO_2$).

4. A light source as recited in claim 2 wherein the layers within the first series have an optical thickness that approximates a quarter-wave.

5. A light source as recited in claim 2 wherein the multilayer dielectric film stack includes a second series of alternating layers of high and low refractive index materials.

6. A light source as recited in claim 5 wherein the layers within the second series of high refractive index materials are composed of magnesium fluoride ($MgF_2$) and the layers within the second series of low refractive index materials are composed of aluminum oxide ($Al_2O_3$).

7. A method of optically inspecting and evaluating a subject comprising the steps of:
  (a) generating a broadband visible light beam;
  (b) generating a broadband ultraviolet light beam;
  (c) combining the visible and ultraviolet light beams using a beam combiner positioned in the path of the visible and ultraviolet light beams, the beam combiner including a multilayer dielectric film stack, the multilayer dielectric film stack being substantially transmissive to light within the visible spectrum so that the broadband visible light beam is transmitted through the combiner, the multilayer dielectric film stack being substantially reflective to light within the ultraviolet spectrum so that the broadband ultraviolet light beam is reflected to follow the visible light beam;
  (d) focusing the combined visible and ultraviolet light beams on the subject; and
  (e) measuring the light reflected from the subject.

8. A method as recited in claim 7 wherein the multilayer dielectric film stack includes a first series of alternating layers of high and low refractive index materials.

9. A method as recited in claim 8 wherein the layers within the first series of high refractive index materials are composed of scandium oxide ($Sc_2O_3$) and the layers within the first series of low refractive index materials are composed of silicon dioxide ($SiO_2$).

10. A method as recited in claim 8 wherein the layers within the first series have an optical thickness that approximates a quarter-wave.

11. A method as recited in claim 8 wherein the multilayer dielectric film stack includes a second series of alternating layers of high and low refractive index materials.

12. A method as recited in claim 11 wherein the layers within the second series of high refractive index materials are composed of magnesium fluoride ($MgF_2$) and the layers within the second series of low refractive index materials are composed of aluminum oxide ($Al_2O_3$).

13. A device for optically inspecting and evaluating a subject, the device comprising:
  (a) a first source for generating a broadband visible light beam;
  (b) a second source for generating a broadband ultraviolet light beam;
  (c) a beam combiner positioned in the path of the visible and ultraviolet light beams, the beam combiner including a multilayer dielectric film stack, the multilayer dielectric film stack being substantially transmissive to light within the visible spectrum so that the broadband visible light beam is transmitted through the combiner, the multilayer dielectric film stack being substantially reflective to light within the ultraviolet spectrum so that the broadband ultraviolet light beam is reflected to follow the visible light beam;
  (d) at least one optical element for focusing the combined visible and ultraviolet light beams on the subject;
  (e) a detector for measuring the light reflected from the subject; and
  (f) a processor for analyzing the measurements made by the detector.

14. A device as recited in claim 13 wherein the multilayer dielectric film stack includes a first series of alternating layers of high and low refractive index materials.

15. A device as recited in claim 14 wherein the layers within the first series of high refractive index materials are composed of scandium oxide ($Sc_2O_3$) and the layers within the first series of low refractive index materials are composed of silicon dioxide ($SiO_2$).

16. A device as recited in claim 14 wherein the layers within the first series have an optical thickness that approximates a quarter-wave.

17. A device as recited in claim 14 wherein the multilayer dielectric film stack includes a second series of alternating layers of high and low refractive index materials.

18. A device as recited in claim 17 wherein the layers within the second series of high refractive index materials are composed of magnesium fluoride ($MgF_2$) and the layers within the second series of low refractive index materials are composed of aluminum oxide ($Al_2O_3$).

19. A light source as recited in claim 1 wherein the layers in the dielectric stack are selected to transmit at least 90% of the broadband visible light and reflect at least 90% of the broadband ultraviolet light.

20. A light source as recited in claim 1 wherein the layers in the dielectric stack are selected to transmit at least 90% of the broadband visible light in the range of 400 to 800 nm and reflect at least 90% of the broadband ultraviolet light in the range of 180 to 350 nm.

21. A method as recited in claim 7 wherein the layers in the dielectric stack are selected to transmit at least 90% of the broadband visible light and reflect at least 90% of the broadband ultraviolet light.

22. A method as recited in claim 7 wherein the layers in the dielectric stack are selected to transmit at least 90% of the broadband visible light in the range of 400 to 800 nm and reflect at least 90% of the broadband ultraviolet light in the range of 180 to 350 nm.

23. A device as recited in claim 13 wherein the layers in the dielectric stack are selected to transmit at least 90% of the broadband visible light and reflect at least 90% of the broadband ultraviolet light.

24. A device as recited in claim 13 wherein the layers in the dielectric stack are selected to transmit at least 90% of the broadband visible light in the range of 400 to 800 nm and reflect at least 90% of the broadband ultraviolet light in the range of 180 to 350 nm.

25. A light source for an optical metrology tool which comprises:
  a first source producing a visible light beam;
  a second source producing an ultraviolet light beam; and
  a beam combiner positioned in the path of the visible and ultraviolet light beams, the beam combiner including a multilayer dielectric film stack, the multilayer dielectric film stack including a first series of alternating layers of high and low refractive index materials wherein the layers within the first series of high refractive index materials are composed of scandium oxide ($Sc_2O_3$) and the layers within the first series of low refractive index materials are composed of silicon dioxide ($SiO_2$), the multilayer dielectric film stack being substantially transmissive to light within the visible spectrum so that the visible light beam is transmitted through the combiner, the multilayer dielectric film stack being substantially reflective to light within the ultraviolet spectrum so that the ultraviolet light beam is reflected to follow the visible light beam.

26. A method of optically inspecting and evaluating a subject comprising the steps of:
 (a) generating a visible light beam;
 (b) generating an ultraviolet light beam;
 (c) combining the visible and ultraviolet light beams using a beam combiner positioned in the path of the visible and ultraviolet light beams, the beam combiner including a multilayer dielectric film stack, the multilayer dielectric film stack including a first series of alternating layers of high and low refractive index materials wherein the layers within the first series of high refractive index materials are composed of scandium oxide ($Sc_2O_3$) and the layers within the first series of low refractive index materials are composed of silicon dioxide ($SiO_2$), the multilayer dielectric film stack being substantially transmissive to light within the visible spectrum so that the visible light beam is transmitted through the combiner, the multilayer dielectric film stack being substantially reflective to light within the ultraviolet spectrum so that the ultraviolet light beam is reflected to follow the visible light beam;
 (d) focusing the combined visible and ultraviolet light beams on the subject; and
 (e) measuring the light reflected from the subject.

27. A device for optically inspecting and evaluating a subject, the device comprising:
 (a) a first source for generating a visible light beam;
 (b) a second source for generating an ultraviolet light beam;
 (c) a beam combiner positioned in the path of the visible and ultraviolet light beams, the beam combiner including a multilayer dielectric film stack, the multilayer dielectric film stack including a first series of alternating layers of high and low refractive index materials wherein the layers within the first series of high refractive index materials are composed of scandium oxide ($Sc_2O_3$) and the layers within the first series of low refractive index materials are composed of silicon dioxide ($SiO_2$), the multilayer dielectric film stack being substantially transmissive to light within the visible spectrum so that the visible light beam is transmitted through the combiner, the multilayer dielectric film stack being substantially reflective to light within the ultraviolet spectrum so that the ultraviolet light beam is reflected to follow the visible light beam;
 (d) at least one optical element for focusing the combined visible and ultraviolet light beams on the subject;
 (e) a detector for measuring the light reflected from the subject; and
 (f) a processor for analyzing the measurements made by the detector.

* * * * *